US00PP08763P

United States Patent [19]

Mantel

[11] Patent Number: Plant 8,763

[45] Date of Patent: May 31, 1994

[54] LILY PLANT LILIUM "GRANDVIEW"

[76] Inventor: Homme Mantel, 15361 SE. Bluff Rd., Sandy, Oreg. 97055

[21] Appl. No.: 99,827

[22] Filed: Jul. 30, 1993

[51] Int. Cl.[5] ..... A01H 5/00

[52] U.S. Cl. ..... Plt./87.4

[58] Field of Search ..... Plt. 27.4

[56] Reference Cited

U.S. PATENT DOCUMENT

PLT 6440 12/1988 Schenk ..... PLT/87.4

*Primary Examiner*—David T. Fox

[57] ABSTRACT

A new variety of hybrid lily plant bearing large upfacing flowers of excellent form and long persistence, both on the plant and as cut-flowers. The pastel orange flowers of the new hybrid are particularly characterized by their tiny, pollen-free anthers and their starry form, with all tepals approximately the same width. This combination is completely new in the Asiatic hybird divisions of lilies suited to forcing and to mass commercial cultivation. The variety is resistant to fusarium disease and shows tolerance of virus. The bulbs may be precooled and forced for cut-flower production. The clone is vigorous and is a good grower and propagator.

1 Drawing Sheet

BACKGROUND OF THE INVENTION

My new variety of lily plant originated as a seedling which first flowered in 1986 in't Zandt, the Netherlands. The breeding efforts had as their objective the production of Asiatic hybrid lilies with upfacing, large-sized pollen-free flowers, suited to forcing into flower out of season, heretofore unknown in the lily breeding art. I achieved the desired objective by intercrossing a small-flowered, pollen-free white upfacing unnamed seedling with a tall, exceptionally vigorous, large-flowered orange unnamed seedling. Both parents were produced by me and never released. The seed parent for 'Grandview' was a pollen-free, albino-flowered mutant Asiatic hybrid produced by open-pollination of 'Sunkissed' (unpatented). 'Sunkissed' was commercially available as a garden lily during the 1970's. The pollen parent for 'Grandview' was produced by open pollination of 'Chinook' (unpatented). 'Chinook' was grown commercially in the United States and the Netherlands as a garden lily and cutflower variety during the 1970's and 1980's.

The flowers of my new lily are characterized by large, upfacing peach to pastel orange flowers with tiny, pollen-free anthers. The flowers have an unusual starry form, with all tepals approximately the same width. In addition, the clone possesses to a high degree desirable characteristics of hybird vigor. The clone is a good grower and propagator, as observed at 't Zandt, the Netherlands.

My new variety of lily plant has been asexually reproduced by me and under my direction at 't Zandt, the Netherlands. Successive generations produced by natural propagation from bulblets, by bulb scale propagation, and by tissue culturing from bulb scale explants have demonstrated that the novel and distinctive characteristics of my new variety are fixed and hold true under asexual propagation from generation to generation.

DESCRIPTION OF THE DRAWING

My new variety of lily plant is illustrated in the accompanying photographic drawing, which shows the open bloom in full color and illustrates the starry flower form with all tepals approximately the same width, the tepal arrangement, and in particular the novel and distinctive tiny, pollen-free anthers.

DESCRIPTION OF THE NEW VARIETY

The following is a detailed description of my new variety of Asiatic hybird lily, with nomenclture according to the *International Lily Register* (The Royal Horticultural Society of London, Second Edition, 1969), and with color designations according to The Colour Chart of The Royal Horticultural Society, published by the Society in 1966.

The Plant

Origin: Seedling.

*Seed parent.*—Unnamed white pollen-free seedling.

*Pollen parent.*—Unnamed tall orange seedling.

Commercial classification: Hybrid *Lilium* clone.

Horticultural classification: Division I-A, Upfacing Asiatic Hybird Lily, according to the Horticultural Classification of Lilies, The Royal Horticultural Society of London.

Form: Single stem, erect and stately.

Height: 1.25 to 1.75 m from bulbs 12 to 16 cm in circumference, provided their light levels are adequate; low light levels may cause "stretching".

Growth: Vigorous and upright.

Foliage quantity: Abundant.

Size of leaf: 7 to 12 cm long, 2 to 4 cm wide.

Shape of leaf: Lanceolate (pointed).

Texture: Leathery and glossy.

Color: Medium to dark green, lighter on lower side.

Bulb size: Any size, ranging to 25 cm circumference commercially.

Bulb color: White, with flushes of pink or yellow after exposure to light.

The Bud

Form: Obtuse, ovoid, and long.

Size: 7 to 10 cm long and 7 to 12 cm in circumference just prior to opening.

Opening: Bud opens slowly, in response to morning light, this takes about one hour.

Color: R.H.S. Colour Chart Orange 25 D, with green tips just prior to opening. Peduncle: Averages 5 to 10 cm, but it may elongate if light levels are too low, if bulbs have been improperly stored prior to forcing, or if bulbs are very large, producing an unusually been improperly stored prior to forcing, or if bulbs are very large, producing an unusually large inflorescence. Color is deep plum over green, appearing almost black to the eye.

The Flower

Blooming habit: Annually in midseason; flowers once and profusely.

Size: Flower are large, averaging 12 to 16 cm in diameter, flattening slightly at the tips on the second day to 12 to 15 cm in diameter. All tepals are approximately 2.5 to 3 cm wide.

Borne: In a signal racemic inflorescence producing 8 to 12 flowers from a bulb 12 to 16 cm in circumference. Large bulbs produce an inflorescence with secondary buds, borne on vertical pedicels.

Shape: Starry, with all tepals approximately the same width and recurving only very slightly at the tips.

Tepalage: Typical of genus *Lilium,* with 6 imbricated tepals.

Tepal color: R.H.S. Colour Chart Orange 25 C/D to Orange-Yellow 23 C/D. Color is deepest at the base of each tepal. Nectaries vary from palest green to ivory under low light conditions and are soft orange when grown under bright light. Nectaries are pubescent, with short white hairs noticeable when the flower is completely open.

Tepal spotting: The basal one-third of the tepals is very lightly spotted with small deep magenta spots, in the area parallel to the nectaries.

Tepal longevity: Tepals stay on stems about three weeks.

Pedicel length: Average 7 to 10 cm long.

Pedicel color: Dark green with deep plum overlay; appear almost black to the eye.

Pedicel form: Sturdy and ascending. Large inflorescences may carry many secondary buds, in which case the pedicels are vertical.

Color changes: Flowers become slightly more peach-toned (more orange and less yellow-gold) as the flowers age. Low light levels and extreme heat may cause them to become lighter but slightly more yellow-orange.

Appearance: Flower is shiny.

Disease resistance: The flower and plant are resistant to disease; in particular, they are resistant to Fusarium bulb rot and Botrytis blight.

Fragrance: None.

Lasting quality: The flower is long lasting, both on the plant and as a cut-flower.

The Reproductive Organs

Stamens: Arrangement typical of genus *Lilium*. Six stamens with R.H.S. Colour Chart orange 27 B filaments 4 to 7 cm long.

Anthers: Tiny (1–4 mm in length), light grey. Anthers do not dehisce.

Pistil: One in number, very soft apricot (R.H.S. Colour Chart orange 27 C/D), 4 to 9 cm long Stigma: Soft plum (R.H.C. Colour Chart greyed purple 185 C/D) in color, large in size.

Characteristics of ovary: Characteristic of genus *Lilium.*

The Fruit

Fertility: The fruit bears a fertile seed.

Shape: Ovoid.

Color at maturity: Soft brown, overlaid with soft plum.

My new variety of Asiatic hybrid lily most nearly resembles 'Chinook,' but it has a pollen-free flowers of a starrier form, much darker stems, and many vertical secondary buds.

I claim:

1. A new and distinctive variety of Asiatic hybrid lily plant substantially as herein shown and described, characterized by its high resistance to disease, its tolerance of virus; its vigorous growth and rapid natural propagation; the excellence of its flower form, size, and substance; its versatility both as a garden plant and as a cut-flower produced from pre-cooled bulbs forced under glass out of season; and in particular by its unique upfacing, pastel orange pollen-free, starry flowers with tepals all approximately the same width, a combination unique among hybrid lilles suited to forcing and to mass commercial cultivation.

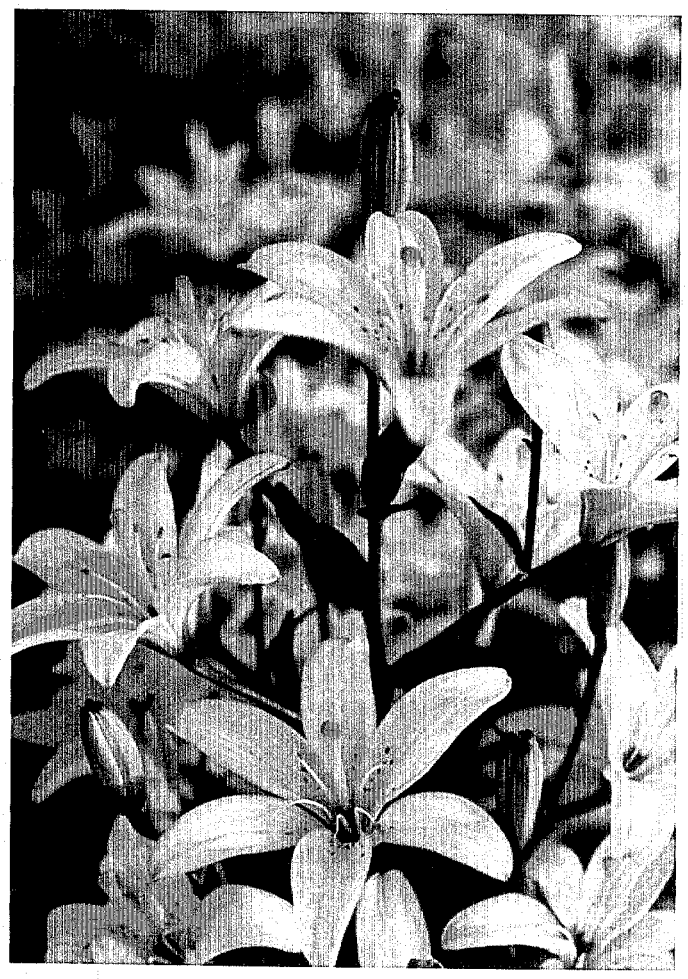

* * * * *